(12) United States Patent
Gyongyossy-Issa et al.

(10) Patent No.: US 7,989,159 B2
(45) Date of Patent: Aug. 2, 2011

(54) PLATELET ADDITIVE SOLUTION WITH A VISCOSITY OF 1.128-1.228 CENTIPOISE @ 37C COMPRISING HYDROXYETHYL STARCH AND METHODS OF MAKING AND USING

(75) Inventors: Maria I. C. Gyongyossy-Issa, Vancouver (CA); Jerry Gongdu Zhang, Surrey (CA)

(73) Assignee: Canadian Blood Services, Ottawa, Ontario (CA)

( * ) Notice: Subject to any disclaimer, the term of this patent is extended or adjusted under 35 U.S.C. 154(b) by 837 days.

(21) Appl. No.: 11/888,003

(22) Filed: Jul. 31, 2007

(65) Prior Publication Data
US 2008/0044803 A1 Feb. 21, 2008

Related U.S. Application Data

(60) Provisional application No. 60/834,164, filed on Jul. 31, 2006.

(51) Int. Cl.
*A01N 1/02* (2006.01)
(52) U.S. Cl. .......................................................... 435/2
(58) Field of Classification Search .................. None
See application file for complete search history.

(56) References Cited

U.S. PATENT DOCUMENTS

| | | | | |
|---|---|---|---|---|
| 4,004,975 | A | 1/1977 | Lionetti et al. | 195/1.8 |
| 4,473,552 | A | 9/1984 | Jost | 424/101 |
| 4,873,230 | A | 10/1989 | Belzer | 514/60 |
| 5,502,043 | A | 3/1996 | Weidler | 514/60 |
| 6,286,119 | B1 | 9/2001 | Wu | 714/726 |
| 6,613,566 | B2 | 9/2003 | Kandler | 435/372 |
| 7,005,253 | B2 * | 2/2006 | Polyak et al. | 435/1.1 |

FOREIGN PATENT DOCUMENTS

| WO | WO 96/17514 | | 6/1996 |
|---|---|---|---|
| WO | WO 03/000052 | * | 1/2003 |

OTHER PUBLICATIONS

Rock et al., "An in vitro method for predicting the efficacy of WBC separation using different starch preparations and anticoagulant ratios", Transfusion 40 (12) : 1442-1445 (2000), abstract only.*
Kainthan et al., "Blood compatibility of novel water soluble hyperbranched polyglycerol-based multivalent cationic polymers and their interaction with DNA," Biomaterials. vol. 27 pp. 5377-5390 (2006).
Gulliksson et al. Defining the optimal storage conditions for the logn-term storage of platelets. Transfusion Medicine Reviews, vol. 17, No. 3, (2003), pp. 209-215.
Gulliksson et al. Platelet storage media. Transfusion and Apheresis Science, vol. 24, (2001), pp. 241-244.
Ringwald et al. The new generation of platelet additive solution for storage at 22°C: Development and Current Experience. Transfusion Medicine Reviews, vol. 20, No. 2, (2006), pp. 158-164.
Ringwald et al. Heyperconcentrated platelet stored in additive solution: aspects on productivity and in vitro quality. Vox Sanguinis, vol. 89, (2005), pp. 11-18.
Ringwald et al. Hyperconcentrated platelets with new additive solutions: aspects on the in vitro quality after 48 hours of storage. Transfusion, vol. 46, (2006), pp. 236-243.
Maguire et al. Function and morphology of platelets produced for transfusion by intermittent-flow centrifugation plateletpheresis or combined platelet-leukapheresis. Transfusion, vol. 21, No. 1, (1981), pp. 118-123.
Strauss et al. Combined platelet-leukapheresis: a technique for preparing separate platelet and granulocyte-platele units from single donors. Transfusion, vol. 19, No. 2, (1978), pp. 206-209.
Van der Meer et al. Comparison of two platelet additive solutions. Transfusion Medicine, vol. 11, (2001), pp. 193-197.
Gullikson et al. Additive solutions for the storage of platelets for transfusion. Transfusion Medicine, vol. 10, (2000), pp. 257-264.
Sputtek et al. Cryopreservation of human platelets with hydroxyethyl starch in a one-step procedure. Cryo-Letters, vol. 8, (1987), pp. 42-46.
Huestis et al. An alternative macromolecular agent for centrifugal leukapheresis. Transfusion, vol. 25, (1985), pp. 343-348.
Eichler et al. Component removal from whole blood by means of gravity sedimentation. Beitr Infusionsther Transfusionsmed, vol. 32, (1994), pp. 12-15.
Bakaltcheva et al. Effects of high-molecular-weight cryoprotectants on platelets and the coagulation system. Cryobiology, vol. 40, (2000), pp. 283-293.
Adkins et al. Hydroxyethylstarch sedimentation by gravity ex vivo for red cell reduction of Granulocye apheresis Components. Journal of Clinical Apheresis, vol. 13, (1998), pp. 56-61.
Van der Meer et al., "Storage of platelets in additive solutions: a pilot in vitro study of the effects of potassium and magnesium," Vox Sanguinis, vol. 82, pp. 131-136 (2002).

* cited by examiner

*Primary Examiner* — Sandra Saucier
(74) *Attorney, Agent, or Firm* — Jenkins, Wilson, Taylor & Hunt, P.A.

(57) ABSTRACT

Disclosed is a platelet additive solution (PAS) comprising a viscosity increasing agent. The use of a PAS comprising such a viscosity increasing agent, especially at concentrations effective to achieve a viscosity similar to that of blood plasma, promotes platelet recovery during extraction from pooled buffy coats and provides for easier platelet production by maintaining the red cell/platelet-rich-supernatant interface.

23 Claims, 7 Drawing Sheets

PLATELET ADDITIVE SOLUTION WITH A VISCOSITY OF 1.128-1.228 CENTIPOISE @ 37C COMPRISING HYDROXYETHYL STARCH AND METHODS OF MAKING AND USING

CROSS-REFERENCE TO RELATED APPLICATIONS

This application claims priority from U.S. Provisional Application No. 60/834,164, filed Jul. 31, 2006, the entirety of which is herein incorporated by reference.

FIELD OF THE INVENTION

The present invention relates to platelet additive solutions, and particularly, to a platelet additive solution which facilitates the preparation of pooled platelet concentrates.

BACKGROUND OF THE INVENTION

Platelets, or thrombocytes, are the constituents of whole blood that form platelet plugs that seal damaged blood vessels and also participate in the mechanisms leading to the formation of blood clots.

People with certain diseases like thrombocytopenia, leukemia, and other cancers, either as a consequence of the disease itself, or of the chemotherapy to treat the cancer, have a reduced number of platelets in their bloodstreams, and without adequate platelets, they bleed abnormally and bruise easily. Regular platelet transfusions are thus essential treatment for these and other patients.

Platelets must be obtained from whole blood donations, typically by separation of the whole blood components via gravitational force in a centrifuge. The force of the centrifuge causes the whole blood to separate based on cell density. The upper layer captured in the centrifuge is plasma. The middle layer is the buffy coat. The bottom, heaviest layer is packed red blood cells. The majority of platelets collected in this way are found in the buffy coat layer. To extract as many platelets as possible, buffy coats are pooled from several donations and re-spun in a centrifuge to separate the platelets from the rest of the buffy coat.

The platelet concentrates are suspended in a liquid, such as plasma. However, while effective as a platelet storage medium, plasma is a valuable blood component that can be used or further processed to purify proteins for use for the treatment of patients with other disorders.

Platelet additive solutions (PAS) have been under development for decades as an alternate platelet suspension and storage medium (for review see Ringwald et al., Transfusion Medicine Reviews 20(2):158-164, 2006a), and apart from making more plasma available for other purposes, they have certain notable advantages. In particular, the use of PASs has been shown to support platelet storage, reduce allergic and febrile transfusion reactions, facilitate ABO-incompatible platelet transfusions, and has more recently been used in conjunction with certain pathogen inactivation methods.

A number of PASs have been described, such as those disclosed in U.S. Pat. No. 6,613,566 (Kandler et al.), and by van der Meer et al. (Transfusion Medicine 11:193, 2001), Gullikson (Transfusion Medicine 10:257-264, 2000), Ringwald et al., 2005 (Vox Sanguinis 89:11-18, 2005), Ringwald et al., 2006b (Transfusion 46:236, 2006) and Ringwald et al. 2006a (supra). PASs are generally known to comprise sodium chloride, sodium citrate and sodium acetate. Alternative PAS have also included phosphate, potassium and magnesium.

Using the currently known PAS formulations, platelet production from centrifuged pooled buffy-coats by semi-automated blood component extractors is difficult. The necessary low speed centrifugation used to pellet red cells but leave the platelets in the supernatant results in an inherently unstable interface. In a production environment, the required ultra-gentle handling of blood bags with such unstable interfaces slows down blood component production, decreases platelet recoveries, and necessitates repeated centrifugations that jeopardize blood bag integrity.

Since such delicate care must be used, blood component production with known PASs is typically slower than with plasma, with significant economic implications. This makes many blood centers reluctant to utilize is PASs despite their noted advantages.

Surprisingly, the present inventors have observed that the difficulty in working with the traditional PAS formulations can be ameliorated through the addition of a viscous component to the PAS.

SUMMARY OF THE INVENTION

An object of the present invention is thus to provide an improved platelet additive solution which facilitates easier production of pooled platelet concentrates.

As an aspect of the present invention, there is provided a platelet additive solution comprising a viscosity increasing agent.

The viscosity increasing agent may be any viscofier or other agent which increases viscosity in an aqueous solution without decreasing platelet viability. In certain embodiments, the viscosity increasing agent may comprise: colloids, including hydroxyethyl starches (HES), gelatins, and dextrans; blood products, such as albumin, albumin substitutes and cross-linked albumin; crystalloids, including Hartmann's solution, hypertonic or hypotonic dextrose solutions, and hypertonic or hypotonic saline solutions; blood substitutes, including haemoglobin-based oxygen carriers (HBOCs), perfluorocarbon emulsions and liposomes, and liposome-encapsulated haemoglobin; or combinations thereof. In preferred embodiments the viscosity increasing agent is selected from hydroxyethyl starch, methyl cellulose, polyethylene glycol, polyglycidol, human albumin, cross-linked albumin, albumin substitutes and combinations thereof. Particularly preferred viscosity increasing agents include hydroxyethyl starches (HES), such as pentastarch and hetastarch, among which pentastarch is particularly preferred. Also suitable for use in the present invention are commercially available hydroxyethyl starches, such as PENTASPAN™.

The concentration of the viscosity increasing agent in the PAS is preferably selected to yield a PAS viscosity up to approximately the viscosity of blood plasma at 37° C. This facilitates the production of platelet pools in a solution with a viscosity that approximates that of human plasma, and thus advantageously avoids the possibility of increasing the blood volume in the recipient. In an embodiment, the platelet additive solution viscosity ranges from 0.80 centipoise (cp) to 1.228 cp, more preferably from 1.128 cp to 1.228 cp, and is most preferably 1.178 cp. In a preferred embodiment, the viscosity increasing agent comprises pentastarch at an end concentration of between about 0.5%-5% w/v, preferably 2%-3.5% w/v, and more preferably about 2.75% in the buffy coat pool. In an alternate embodiment the viscosity increasing agent is polyglycidol with a concentration ranging from 3.6% to 4.6% w/v, preferably 4.1% w/v.

The platelet additive solution components may comprise at least one energy source, at least one buffering component, at least one chelator, at least one salt component, and optionally, at least one metabolic regulator and at least one membrane polarity stabilizing component, all at effective concentrations. In an embodiment, the platelet additive solution components comprise sodium citrate, sodium acetate, sodium chloride and optionally one or more of Na-gluconate, $NaH_2PO_4$, $Na_2HPO_4$, $MgCl_2$ and KCl, all in effective concentrations.

The at least one salt component is advantageously provided at a concentration sufficient to give a PAS osmolality ranging from 250 mOsm to 400 mOsm, preferably 270 mOsm to 310 mOsm, and more preferably ranging from 290 mOsm to 300 mOsm.

In an embodiment, a viscosity increasing agent-infused platelet additive solution comprises 10.0-10.9 mM $Na_3$Citrate, 27.0-32.5 mM NaAcetate, 69.0-115 mM NaCl, and a concentration of viscosity increasing agent sufficient to give a PAS viscosity ranging from 1.128 centipoise to 1.228 centipoise. When the viscosity increasing agent is pentastarch, the concentration of the pentastarch in preferred embodiments ranges from 2% to 3.5% w/v. When the viscosity increasing agent is polyglycidol, the concentration of the polyglycidol preferably ranges from 3.6% to 4.6% w/v.

The viscosity increasing agent-infused platelet additive solution may be used for collection and/or storage of platelets.

As a further aspect of the invention, there is provided a solution system for preparing platelet concentrates comprising at least one viscosity increasing agent and platelet additive solution components, wherein said viscosity increasing agent and platelet additive solution components are provided in at least one receptacle.

The receptacle will be a container or other receptacle known in the field capable of enclosing a liquid or soluble material, such as a blood bag, a serum bottle, a serum tube, a vial or the like, and in preferred embodiments will be sterile or capable of being sterilized using known methods.

The solution system may comprise one or both of the at least one viscosity increasing agent and platelet additive solution components in aqueous solution or as as a soluble material, either in effective concentrations and/or in suitable dry amounts. In preferred embodiments the aqueous solutions will be sterilized. In select embodiments the viscosity increasing agent and platelet additive solution components are provided as concentrates in one or more separate receptacles in effective concentrations to yield a viscosity increasing agent-infused platelet additive solution with a viscosity ranging from 1.128 centipoise to 1.228 centipoise when combined. Each of the viscosity increasing agent and individual platelet additive solution components can be provided in separate receptacles, either in aqueous or dry forms.

As another aspect, the present invention provides a process for preparing a buffy coat pool in a platelet additive solution comprising viscosity increasing agent, the process comprising the steps of:

a) Sterile docking a concentrated sterile platelet additive solution and a concentrated sterile solution of viscosity increasing agent to one or more prepared buffy coats in blood bags;

b) Draining the buffy coats; and c) Adding the concentrated sterile platelet additive solution and concentrated sterile solution of viscosity increasing agent to the drained buffy coats; whereby the concentrations of the concentrated platelet additive solution and concentrated viscosity increasing agent are selected to yield effective final concentrations of platelet additive solution components and viscosity increasing agent in the resulting buffy coat pool.

In accordance with the above method, the hyperosmotic platelet additive solution is preferably mixed with hypoosmotic (but hyperviscous) viscosity increasing agent such that the platelet additive solution and viscosity increasing agent combine to form a viscosity increasing agent-infused platelet additive solution in the final buffy coat pool diluted to bring the salt content of the platelet additive solution to 100% and the viscosity increasing agent to a final desired concentration which gives a viscosity up to approximately the viscosity of blood plasma at 37° C.

The above method may be adapted to known Standard Operating Procedures (SOPs) for buffy coat pool production, for instance using a buffy coat train or octopus arrangement.

BRIEF DESCRIPTION OF THE DRAWINGS

Further features and advantages of the present invention will become apparent from the following detailed description, taken in combination with the appended drawings, in which.

DETAILED DESCRIPTION OF THE PREFERRED EMBODIMENT

The present invention provides a new platelet additive solution having improved platelet recovery performance and production efficiency. This has been achieved through the addition of at least one viscosity increasing agent to the PAS formulation. By increasing PAS viscosity, increased stability of the red cell-platelet rich supernatant interface is achieved, thus improving the ease of handling centrifuged pooled buffy coats.

Figure 1:
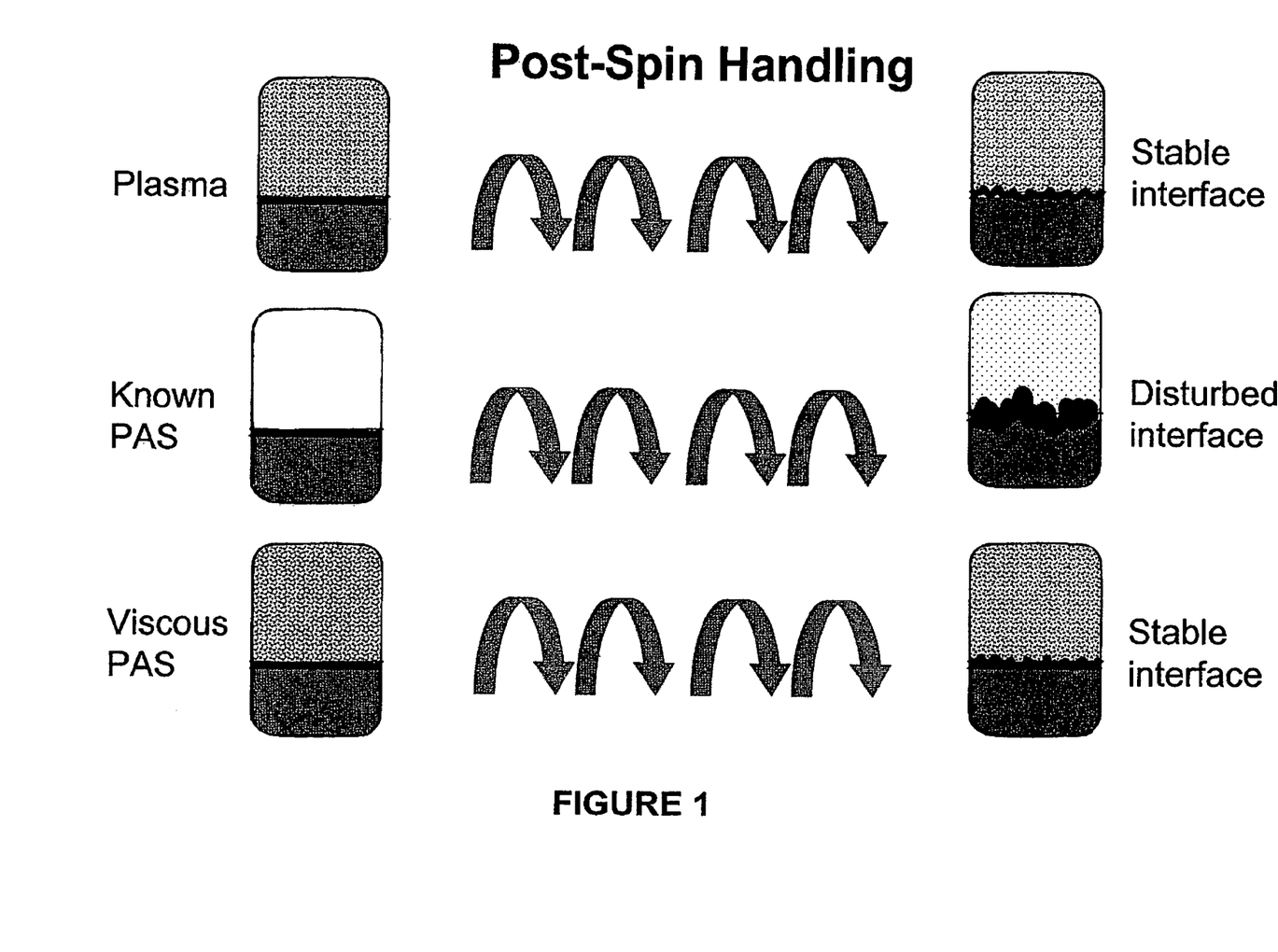
FIG. 1 is a schematic illustration of observed interface stabilities when handling pooled buffy coats pooled in plasma, conventional PAS compositions, and an embodiment of the viscous PAS of the present invention.

As illustrated in FIG. 1, the necessary low speed centrifugation used to pellet red cells but leave the platelets in the supernatant results in an inherently unstable interface when using conventional platelet additive solutions. The left hand side of the illustration denotes buffy-pools at the end of the centrifugation cycle, and the right hand side denotes buffy-pools after handling. Buffy pool handling commonly involves steps such as removing the blood bags from centrifugation buckets, and placement onto blood component processors for processing, e.g. onto a Compomat™ G4 automatic blood component processor. As depicted in the illustration, a disturbed interface is commonly observed when using known platelet additive solutions, whereas more stable interfaces are observed when using a PAS comprising a viscosity increasing agent, similar to the interfaces observed using plasma.

A variety of viscosity increasing agents may be used in accordance with the present invention to increase the PAS viscosity, including hydroxyethyl starches, methyl cellulose, polyethylene glycol (PEG), polyglycidol, human albumin, cross-linked albumin, albumin substitutes and combinations thereof (see for example Gutteridge, G., Crystalloids, colloids, blood, blood products and blood substitutes. Anaesthesia & intensive care medicine, Volume 5, Issue 2, Pages 42-46, incorporated herein by reference). However, hydroxyethyl starches are particularly useful due to their known clinical effectiveness and utility in the preparation of blood products. Preferred hydroxyethyl starches for use in accordance with the present invention include pentastarch and hetastarch, of which pentastarch is particularly preferred.

Pentastarch is commercially available under the product name PENTASPAN™ (Bristol-Myers Squibb), which comprises 10% pentastarch. PENTASPAN™ is a known plasma volume expander which is employed in vivo for plasma volume expansion.

In chemical terms, pentastarch is defined as a low molecular weight, low molar substitution hydroxyethyl starch, and is an artificial colloid derived from a waxy starch composed predominantly of amylopectin. Hydroxyethyl groups are introduced into the glucose units of the starch and the resultant material is hydrolyzed to yield a product with a molecular weight of about 200,000-300,000. The degree of substitution is about 0.40-0.50 which means pentastarch has approximately 45 hydroxyethyl groups for every 100 glucose units.

Particularly useful are platelet additive solutions comprising a viscosity increasing agent in an amount effective to give a PAS viscosity similar to that of plasma. Plasma viscosity was measured to be 1.178 centipoise at 37° C., although plasma viscosities are known to vary amongst people depending on the amount of fluid gain/loss. Accordingly, a particularly preferred viscosity of the PAS in accordance with the present invention is 1.178+/−0.05 centipoise, at the same temperature. It is to be understood, however, that PAS viscosities lower than this preferred viscosity range may be used in accordance with the present invention with platelet production benefits increasing up to the aforesaid preferred viscosity value. The use of platelet additive solutions with viscosities substantially greater than that of human plasma may yield platelet concentrates which increase blood volume in the recipient, causing potential clinical implications, and such PAS viscosities should be therefore preferably avoided for clinical applications.

Together with a viscosity increasing agent, the platelet additive solution of the present invention may comprise any combination of PAS ingredients. Accordingly, the constituents and concentrations of the platelet additive solution of the present invention may vary. Platelet additive solutions of the present invention preferably comprise, together with at least one viscosity increasing agent, an energy source, a buffering component, and a chelator. In select embodiments, this may involve sodium chloride, sodium citrate and sodium acetate, together with the viscosity increasing agent. Phosphate, potassium and magnesium may also be provided in effective concentrations. The following table outlines the salt concentrations in three commercially available platelet additive solutions, which lack viscosity increasing agent.

TABLE 1

Salt concentrations in commercially available Platelet Additive Solutions.

| | T-Sol(mM) (Baxter Healthcare) | Composol ™ (mM) (Fresenius Kabi) | SSP+ (mM) (MacoPharma) |
|---|---|---|---|
| $Na_3Citrate$ | 10.0 | 10.9 | 10.8 |
| NaAcetate | 30.0 | 27.0 | 32.5 |
| NaCl | 115 | 90.0 | 69.0 |
| NaGluconate | — | 23.0 | — |
| $Na_2HPO_4$ | — | — | 21.5 |
| $NaH_2PO_4$ | — | — | 6.7 |
| $MgCl_2$ | — | 1.5 | 1.5 |
| KCl | — | 5.0 | 5.0 |

A platelet additive solution formulation according to the present invention may comprise: 10.0-10.9 mM $Na_3Citrate$, 27.0-32.5 mM NaAcetate, 69.0-115 mM NaCl, and sufficient viscosity increasing agent to give a PAS viscosity of 1.178+/−0.05 centipoise, e.g. approximately 2.75% pentastarch w/v. The PAS may also optionally comprise one or more of Na-gluconate (0-40 mM), $NaH_2PO_4$ (0-40 mM), $Na_2HPO_4$ (0-20 mM), $MgCl_2$ (0-20 mM), and KCl (0-20 mM).

A preferred PAS composition in accordance with the present invention comprises: 10.8 mM $Na_3Citrate$, 32.5 mM NaAcetate, 69.0 mM NaCl, 6.7 mM $NaH_2PO_4$, 21.5 mM $Na_2HPO_4$, 1.5 mM $MgCl_2$, 5.0 mM KCl, and 2.75% pentastarch w/v.

Experiments:
i) Optimization of PAS Based On Viscosity

Figure 2:
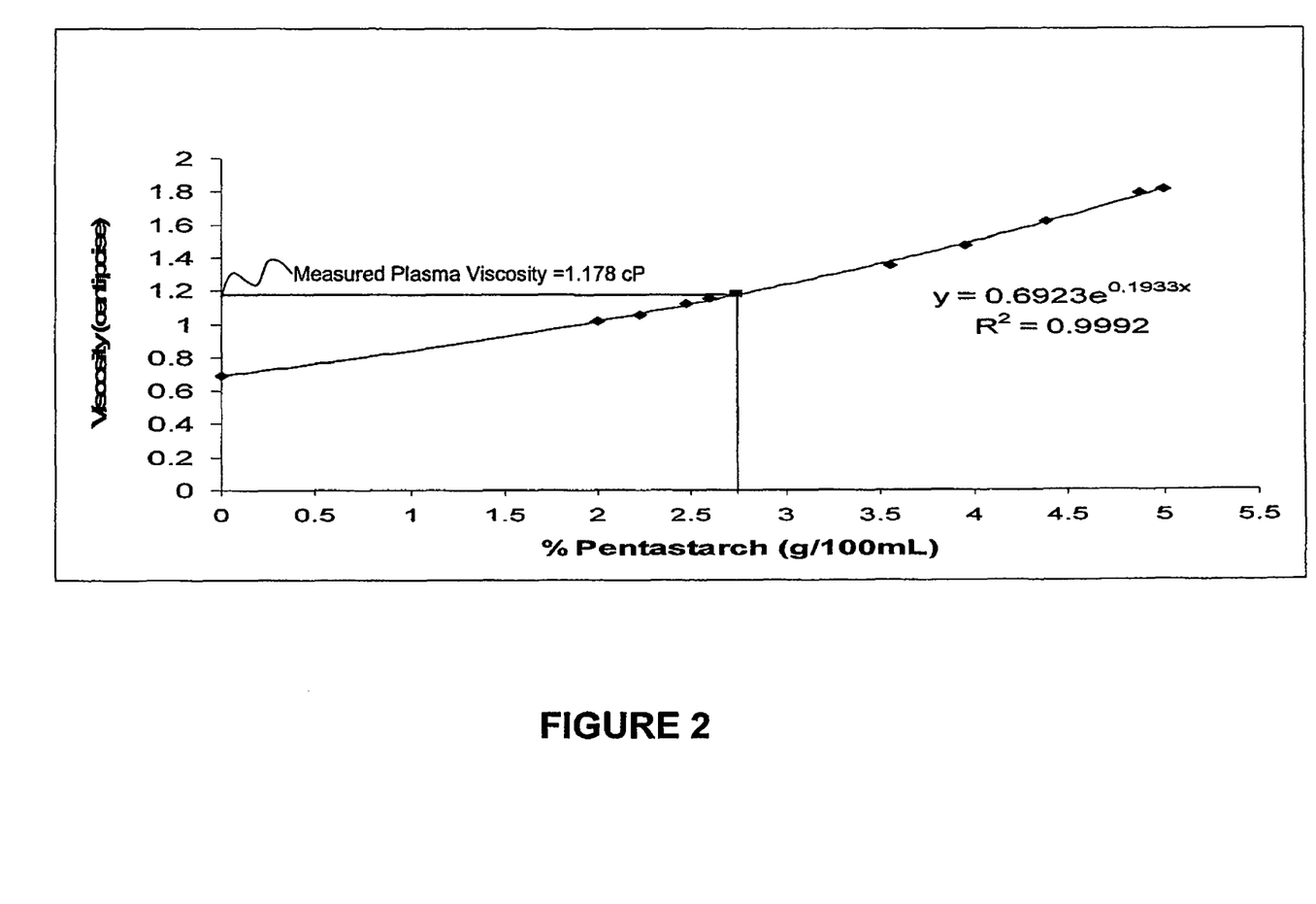
FIG. 2 is a plot of viscosity measured as a function of pentastarch concentration at 37° C.

Plasma viscosity ranges as found in normal blood bags designed for buffy coat component production methods were measured to be 1.178 cp. Using a range of dilutions and standard curves, the optimal viscosity of pentastarch that would match the viscosity of plasma was calculated (FIG. 2). By testing a range of pentastarch concentrations around the calculated optimal viscosity value it was established that approximately 2.75% pentastarch mimicked plasma viscosity.

The G forces that would give an optimal platelet yield from a buffy coat pool in a platelet additive solution comprising 2.75% pentastarch was determined. In the present example, the 2.75% pentastarch buffy coat pools were in SSP+ (115.5 mM NaCl, 10.0 mM $Na_3Citrate$ and 30.0 mM NaAcetate) including 2.75% pentastarch and residual plasma, which is set by the process itself to contain 20%-30% residual plasma. This level of residual plasma is what is reported to be ideal for platelet additive solutions.

Figure 3:
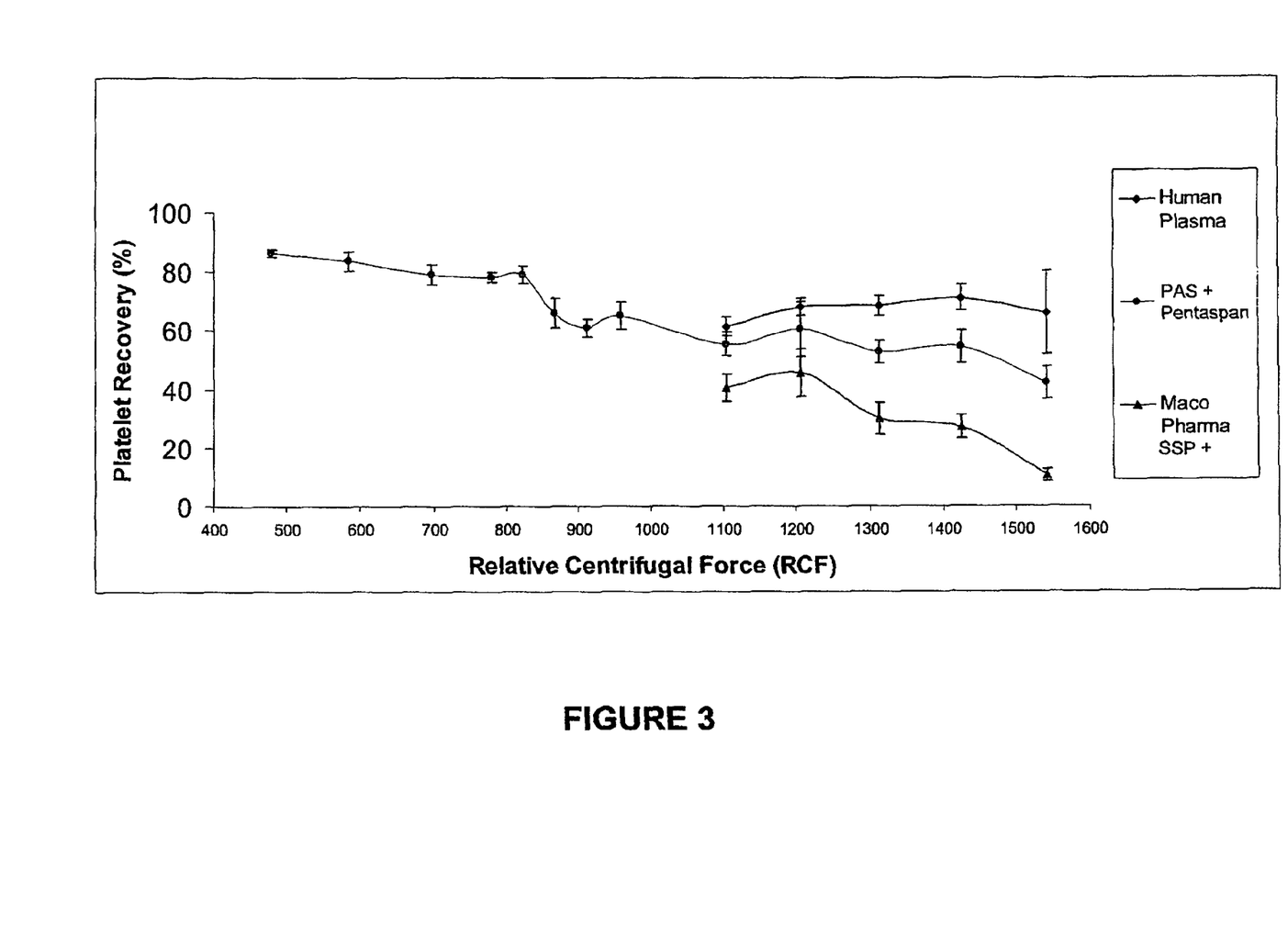
FIG. 3 is a plot of platelet recovery measured as a function of relative centrifugal force for human plasma, pentastarch-infused PAS and pentastarch-free PAS (MacoPharma SSP+).

As can be seen in FIG. 3, the platelet additive solution comprising 2.75% pentastarch gives a reproducible platelet recovery of 80±5% at normal blood component production scale, i.e. a manufacturing scale typical of blood centers, using a Sorvall RC3BP centrifuge. In brief, the experiments begin with full units (480 mL-500 mL) of whole blood using equipment and bag systems standard for an actual production setting to yield transfusable blood components (RBCs, plasma, platelet concentrate). Centrifuge parameters were: R=277 mm, 1625 RPM for 5 min, RCF: 823 g, slow start 9, slow stop 3. This result compares favourably to the normal production yield obtained using human plasma instead of the pentastarch infused PAS, which resulted in 77±5% platelet recovery at the optimal centrifuge setting for plasma (1233 RCF). Platelet recoveries for pentastarch-free MacoPharma SSP+ were routinely 40-50% at the optimal plasma RCF values and consistently lower than the pentastarch-infused PAS solution.

ii) Preparation of Buffy Coat Pools in Viscosity Increasing Agent-Infused PAS

In the following, pentastarch was used as an exemplary viscosity increasing agent for the preparation of a buffy coat pool in a viscous platelet additive solution. The methods described are further provided as exemplary embodiments of the method of the present invention.

First, the desired platelet additive solution was prepared as a concentrated solution, in the present example as a 137.9% w/v solution, and steam sterilized. The concentrations of the PAS components in the final 100% solution were: 10.8 mM $Na_3$Citrate, 32.5 mM NaAcetate, 69.0 mM NaCl, 6.7 mM $NaH_2PO4$, 21.5 mM $Na_2HPO_4$, 1.5 mM $MgCl_2$ and 5.0 mM KCl, and thus all of the aforesaid concentrations were multiplied by 1.379 for the 137.9% solution. The steam sterilized solution (217.5 mL) was dispensed into a top-and-bottom (T&B) blood component preparation bag. Concentrated pentastarch solution (10% w/v) was prepared in water, filter sterilized, and 82.5 mL of the concentrated sterile solution was dispensed into a 100 mL infusion bag. The bags were then assembled into a train as illustrated in FIG. 4.

Figure 4:
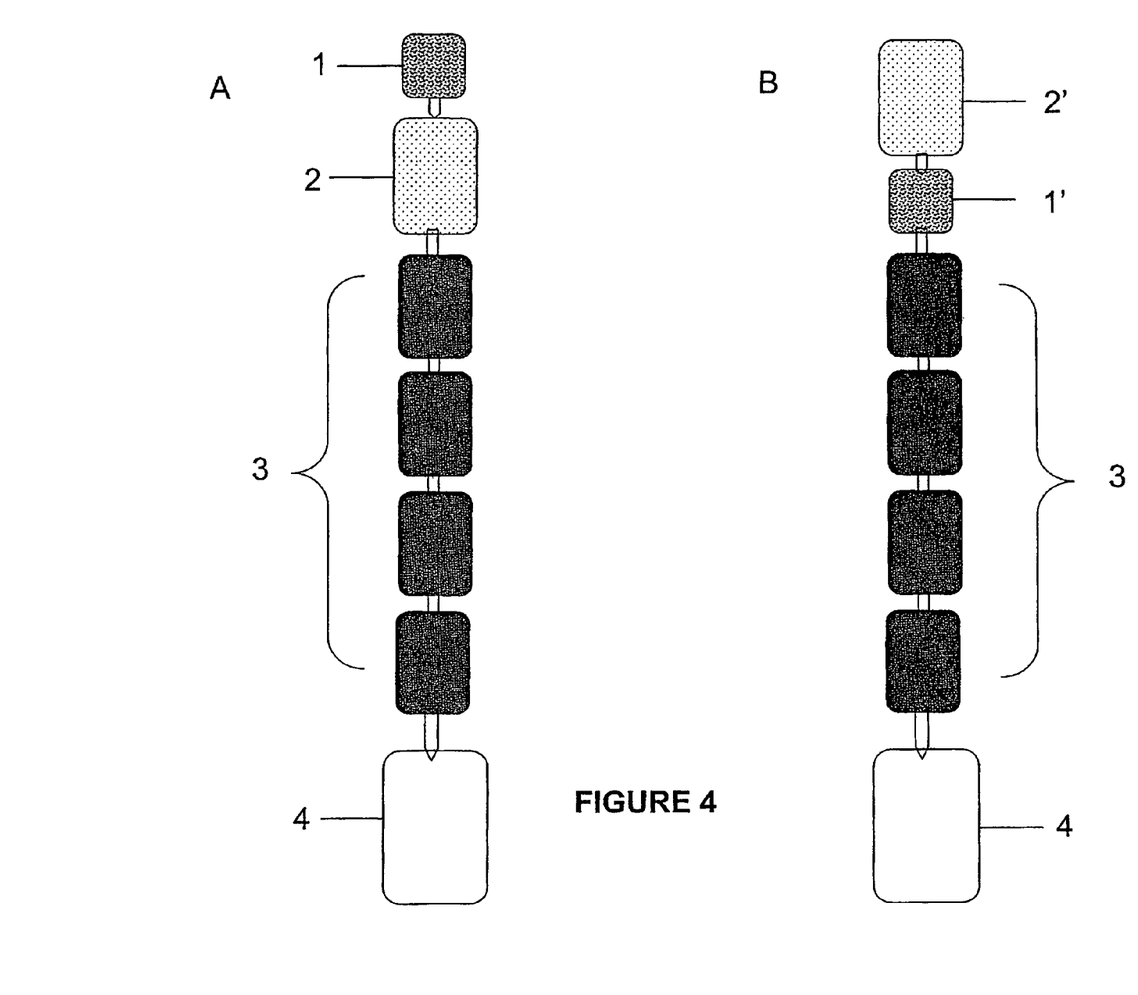
FIG. 4 is a schematic illustration of an exemplary embodiment of the method of the present invention, illustrating a "buffy-train system" for buffy-coat production with reversible setup of the connection of hypertonic PAS solution and concentrated viscosity increasing agent.

In FIG. 4A, the pentastarch infusion bag 1 is sterile docked to the top of the T&B concentrated PAS bag 2. The bottom of the T&B concentrated PAS bag 2 is in turn sterile docked to the top of a "buffy coat train" 3 prepared by sterile docking four buffy coats prepared in blood bags using known standard operating procedures (SOPs). A platelet storage bag 4 is docked at the bottom of the train. Certain other SOPs prescribe the assembly of five or more buffy coat bags in a train, and thus the number of buffy coat bags can be varied with the amount of viscosity increasing agent being added in proportion to the PAS and the number of buffy coats pooled.

The above-described setup involves attaching two bags, one containing concentrated pentastarch and one containing concentrated PAS, to the top of a buffy coat train. In this embodiment, the bag immediately preceding the buffy coats needs to be a top and bottom bag to allow for docking to the buffy-coat train 3 below and to the bag above, regardless of whether the concentrated PAS or pentastarch is first or second in the train. In an alternate embodiment, as shown in FIG. 4B, the order may be reversed such that the pentastarch is provided in a T&B bag 1' immediately preceding the buffy coat train 3, with a concentrated PAS bag 2' docked at the top of the pentastarch T&B bag 1'.

Figure 5:
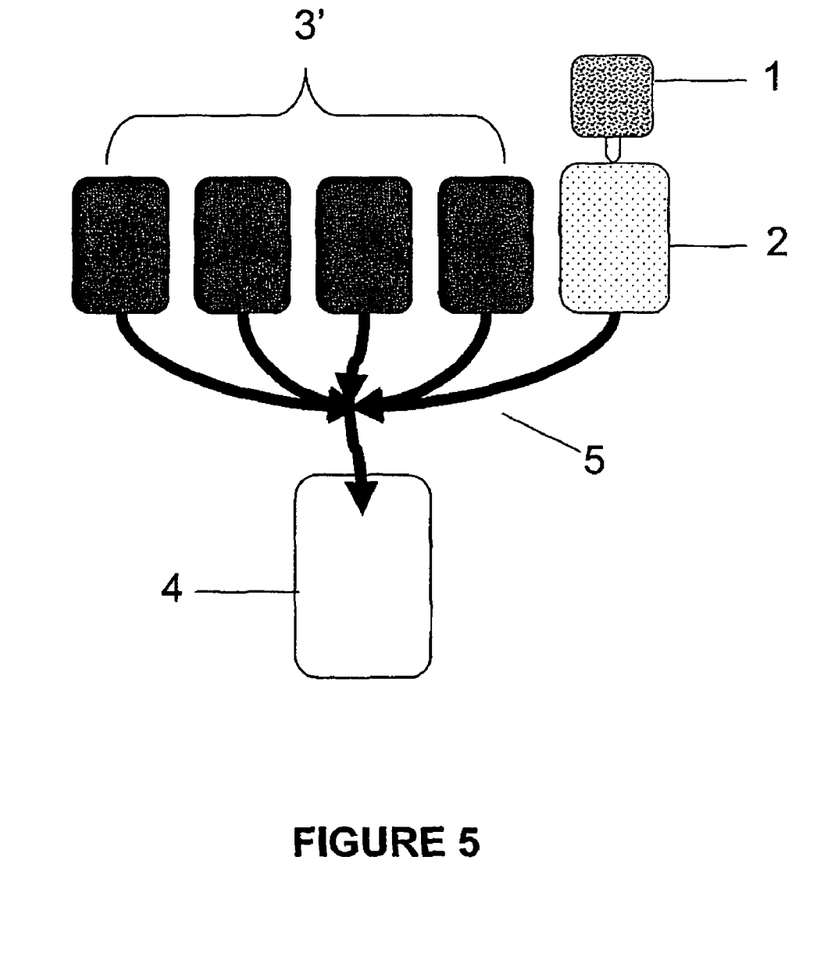
FIG. 5 is a schematic illustration of another exemplary embodiment of the method of the present invention, illustrating an "octopus system" for buffy-coat production.

The setup for adding PAS+viscosity increasing agent may be further varied, provided that the total ingredients are dispensed into the bag 4 to be centrifuged at desired final concentrations. For instance, an "octopus system" as illustrated in FIG. 5 may be used for the buffy-coat production, whereby a pentastarch infusion bag 1 and T&B concentrated PAS bag 2 is sterile docked to a "buffy coat train" 3' via octopus tubing 5. Alternate setups in which the PAS and viscosity increasing agent are added together as a single concentrated solution are also envisioned. Nevertheless, the preferred embodiment is to provide concentrated PAS bag 2' at the top of the train, as depicted in FIG. 4B, with concentrated pentastarch provided below in T&B bag 1', such that all of the viscous solution in the T&B bag 1' is rinsed through by the concentrated PAS from bag 2'.

The buffy coats in the train 3 were allowed to drain into the bottom bag. The concentrated pentastarch solution was then allowed to drain through the train into the concentrated PAS bag 4, and the bag was mixed well. The bags of the buffy coat train were rinsed through to the bottom by allowing the PAS/pentastarch mixture to rinse the intervening bags in two separate washes. The PAS/pentastarch mixture was then mixed well with the buffy coat pool in the bottom bag. Accordingly, the hyperosmotic PAS was diluted with hypoosmotic (but hyperviscous) pentastarch, and the concentrated PAS/pentastarch was diluted into the buffy coat pool/PAS/pentastarch mixture such that the salt content of the PAS was brought to 100% from 137.9% w/v, while the pentastarch was diluted from 10% w/v to a final concentration of 2.75%.

iii) Characterization of Platelets Prepared in Viscous PAS

The final concentrations of the components in the viscous PAS used to prepare the platelet concentrates are outlined in Table 2 below, alongside the starting concentrations of the components in the pentastarch infusion bag 1 (10% Pentaspan™) and the T&B concentrated PAS bag 2 (Hypertonic SSP+).

TABLE 2

Final viscous PAS and starting reagent composition and relative concentrations

| | Viscous PAS (Final) | 10% Pentaspan ™ | Hypertonic SSP+ |
|---|---|---|---|
| $Na_3$Citrate | 10.8 mM | — | 14.9 mM |
| NaAcetate | 32.5 mM | — | 44.85 mM |
| NaCl | 69.0 mM | 154.0 mM | 36.78 mM* |
| NaGluconate | — | — | — |
| $NaH_2PO_4$ | 6.7 mM | — | 9.25 mM |
| $Na_2HPO_4$ | 21.5 mM | — | 29.67 mM |
| $MgCl_2·6H_2O$ | 1.50 mM | — | 2.07 mM |
| KCl | 5.0 mM | — | 6.90 mM |
| Pentastarch 200-300 kDa MW DS 0.55 | 2.75% (% = g/100 mL) | 10% | — |
| pH | 7.20 | ~5.0 | 7.20 |
| Viscosity @ 37° C. | 1.178 ± 0.003 cp | 4.469 ± 0.002 cp | 0.7353 ± 0.0006 cp |

*Note: in hypertonic SSP+, all concentrations in SSP+ are inflated ~139% except NaCl, to account for the high concentration of NaCl already present in Pentaspan ™.

Platelet recoveries were measured for platelet pools prepared in plasma; Composol, SSP+ and TSol (collectively 'PAS' in the tables below); and viscous PAS as defined above including 2.75% pentastarch w/v. The recovery values are outlined in Table 3, followed by statistical analysis results on this data in Table 4.

TABLE 3

Platelet Recovery from Buffy-coat Pool (BCP)

| Storage Medium | Recovery (%) | 95% Confidence |
|---|---|---|
| Plasma (~300 mL) | 73.69 | ±5.92% |
| Platelet Additive Solution (PAS)*** | 64.53 | ±2.06% |
| Viscous PAS | 76.96 | ±2.57% |

***Averaged values obtained using Composol, SSP+, and TSol

TABLE 4

Student's t-test comparison of platelet recoveries (p-values less than 0.05 are considered significant)

| Comparison | p-value | Significance |
|---|---|---|
| Viscous PAS vs. Plasma | 0.363 | Not significant |
| Viscous PAS vs. PAS*** | $9.34 \times 10^{-5}$ | $p \ll 0.05$ |

***Averaged values obtained for Composol, SSP+, and TSol

Platelets prepared in accordance with the method in (ii) above were characterized according to known indicators of platelet viability, the results of which are provided in Table 5.

TABLE 5

Characteristics of Platelet Concentrates (PCs) stored in Plasma vs. Viscous PAS over a seven day period

| | Plasma | | Viscous PAS | |
|---|---|---|---|---|
| | Day 1 | Day 7 | Day 1 | Day 7 |
| Concentration ($10^9$ cells/L) | 830 ± 73 | 840 ± 104 | 837 ± 84 | 782 ± 87 |
| MPV (fL) | 8.28 ± 0.45 | 8.96 ± 0.67 | 9.05 ± 0.30 | 9.1 ± 0.45 |
| Soluble Protein Conc. (mg/mL) | 56.61 ± 6.45 | 56.09 ± 9.20 | 13.47 ± 0.24 | 14.97 ± 1.62 |
| pH | 7.05 ± 0.03 | 7.20 ± 0.24 | 7.07 ± 0.01 | 7.24 ± 0.03 |
| $pO_2$ (mmHg) | 77.4 ± 9.9 | 96.4 ± 15.5 | 70.3 ± 10.2 | 85.0 ± 11.7 |
| $pCO_2$ (mmHg) | 76.2 ± 6.7 | 40.8 ± 19.1 | 28.3 ± 1.5 | 18.0 ± 1.9 |
| Glucose consumption rate (mmol/L·Day) | 0.8447 | | 0.3365 | |
| Lactate production rate (mmol/L·Day) | 1.4258 | | 0.7591 | |
| CD62 Surface Expression (%) | 30.15 ± 3.59 | 58.37 ± 11.71 | 34.08 ± 6.43 | 37.43 ± 3.31 |
| Extent of Shape Change (%) | 21.26 ± 2.10 | 17.88 ± 2.54 | 21.39 ± 4.35 | 15.60 ± 2.33 |
| Hypotonic Shock Response (%) | 53.38 ± 6.21 | 49.79 ± 15.34 | 58.45 ± 7.63 | 75.76 ± 10.95 |
| Morphology | 314 ± 11 | 249 ± 18 | 333 ± 17 | 259 ± 12 |

Concentration: This test is an indicator of whether platelets die in significant quantities. On comparison between day 1 and day 7 for plasma and viscous PAS, there is no significant decrease over the storage period.

Mean Platelet Volume (MPV): This test is a measure of platelet size. This should not fluctuate significantly as decreases may indicate fragmentation. Comparisons between day 1 and day 7 for platelets stored in plasma and viscous PAS show that there were no significant changes in either storage medium, indicating minimal fragmentation.

Soluble Protein Concentration: This test measures the amount of residual plasma there is present in the final platelet concentrate. As well it can indicate major platelet death whereby significant protein increases from day 1 to day 7 denote a significant death rate. In this case, soluble proteins measured in Viscous PAS stored platelets are not significantly different between day 1 and day 7. Similarly, soluble proteins measured in plasma stored platelets are not significantly different between day 1 and day 7 although the plasma protein values may mask any platelet-caused changes.

pH: pH above 7.0 is desirable. In this case, for platelet concentrates stored in plasma and viscous PAS, there is not a significant difference between days 1 and 7.

$pO_2$ and $pCO_2$: These traits are a measure of how well the storage bag performs. Oxygen and $CO_2$ both equilibrate slowly with respect to their atmospheric partial pressures, 176 mmHg and 4 mmHg, respectively. Both are within described ranges for the platelet concentrates stored in plasma and viscous PAS.

Glucose consumption rate: This test is a measure of platelet metabolism, whereby a slower glucose consumption is more desirable. As indicated by the present results, platelets stored in viscous PAS consume glucose at a rate >2 times slower than platelets stored in plasma.

Lactate production rate: This test is another measure of platelet metabolism, again whereby a slower rate leads to better in vivo recovery. As shown, platelets stored in viscous PAS produce lactate at half the rate of platelets stored in plasma.

CD62 Surface Expression: CD62 surface expression is an indicator of platelet activation. Platelet concentrates stored in viscous PAS show significantly lower (p<0.05) activation than platelets stored in plasma.

Extent of Shape Change: Shape change is another indicator of platelet activation. No significant differences are observed between platelet concentrates stored in viscous PAS and plasma on days 1 & 7.

Hypotonic Shock Response: This test is an indicator of platelet integrity shown by their ability to pump out water. Platelet concentrates stored in viscous PAS show significantly better results (p<0.05) on Day 7 when compared to platelet concentrates stored in plasma.

Morphology: A further indicator of platelet activation, no significant differences were observed in the morphology of platelets stored in viscous PAS and plasma on days 1 & 7.

iv) Alternate Viscosity Increasing Agent

A second polymer, polyglycidol, having a mean mass number (Mn) of 160 kDa, was evaluated with respect to its ability to facilitate platelet collection.

Polyglycidol is a polymer with a completely different structural organization relative to HES. HES is ethylated starch, which is linear, while the polyglycidol has a highly branched structure as can be seen in Formula (1) below:

(1)

This polymer has been reported previously (Kainthan R K, Gnanamani M, Ganguli M, Ghosh T, Brooks D E, Maiti S, Kizhakkedathu J N, Blood compatibility of novel water soluble hyperbranched polyglycerol-based multivalent cationic polymers and their interaction with DNA. *Biomaterials*, 2006, 27:5377-90; herein incorporated by reference).

Figure 6:
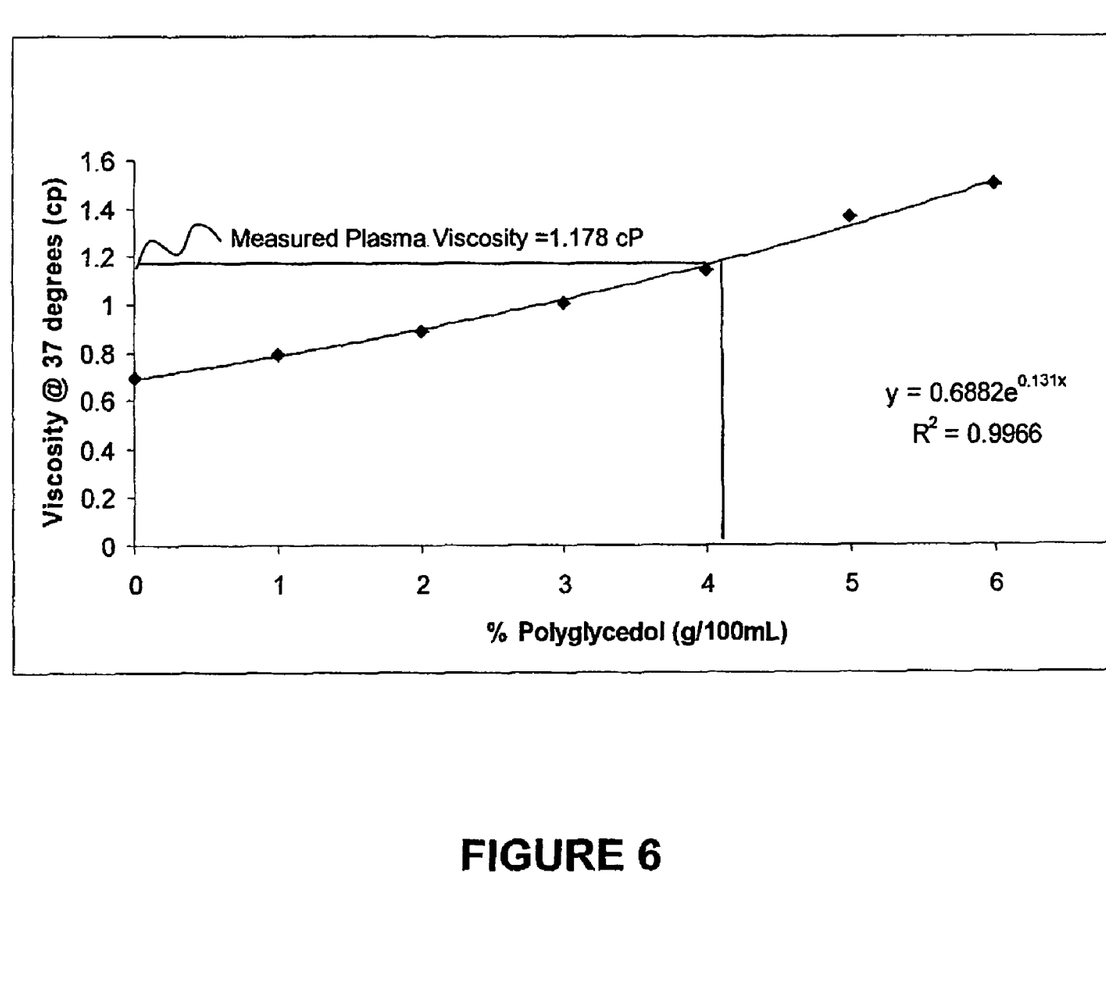
FIG. 6 is a plot of viscosity measured as a function of polyglycidol concentration at 37° C.

Using a range of dilutions and standard curves, the optimal viscosity of polyglycidol that would match the viscosity of plasma was calculated (FIG. 6). As demonstrated, the extrapolated concentration necessary to mimic plasma viscosity is 4.10±0.5%. The relatively large error range in this value is rationalized as being attributable to the randomness of the polymer size of the polymer material available. Industrially engineered polymers will have a more reproducible molecular weight range and hence should give more consistent concentration values.

Figure 7:
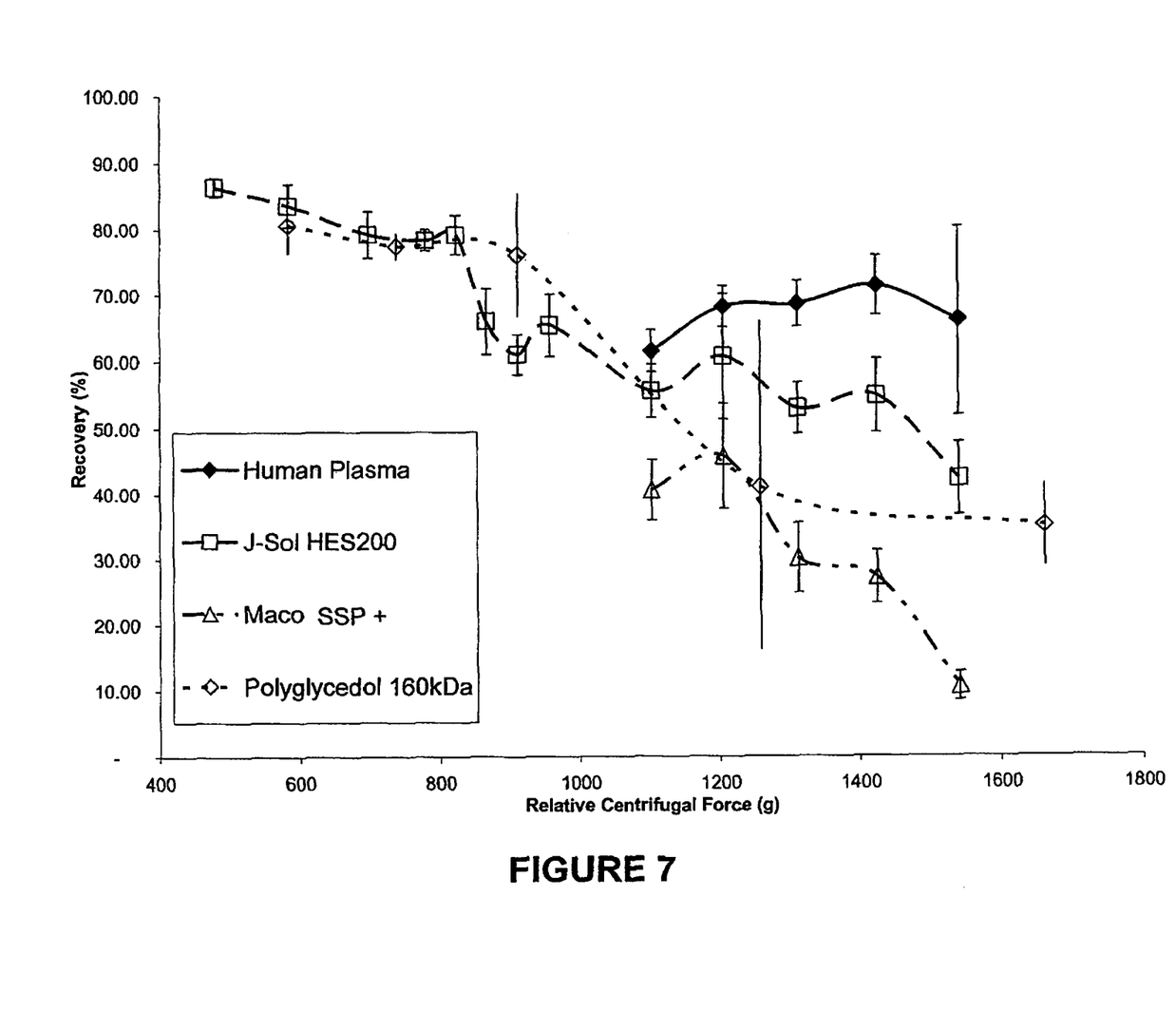
FIG. 7 is a plot of platelet recovery measured as a function of relative centrifugal force for human plasma, pentastarch-infused PAS, pentastarch-free PAS (MacoPharma SSP+) and polyglycidol-infused PAS.

Polyglycidol was dissolved in Baxter T-sol platelet additive solution. This solution was used to extract platelets from buffycoat at the same concentration ratios as per real production (60% viscous PAS, 40% buffycoat, viscous PAS being 4.10% polyglycidols dissolved in Baxter T-sol). The results (FIG. 7) suggested a centrifugation setting of approximately 850-900 RCF for 5 minutes for polyglycidol. The polyglycidol data is shown in FIG. 7 together with the same data shown in FIG. 3 as a means of comparison.

Similarities exist between the results obtained for HES and polyglycidol. However, more RCF is required for polyglycidol due to a lack of intrinsic inability of polyglycidol to precipitate cells. Use of HES alone, even without centrifugation, will result in precipitation of all cells at a rate relative to cell size; polyglycidol does not do this, so a harder centrifugation is needed to pellet the red cells.

The RCF range (850-900×g) was scaled to industrial centrifuge parameters for blood component separation using a Beckman RC3BP centrifuge. 300 mL of viscous PAS with polyglycidol was mixed with 4×50 mL buffy-coats as described earlier. The resultant mix was spun at 2000 rpm, slow start 9, slow stop 3 for 5 min at 22 degrees centigrade. It should be noted that 2000 rpm on this centrifuge converts to 950 RCF. A harder spin was used because the above-described experiments (shown in FIG. 7) are done in rigid test tubes whereas the blood on a production scale are spun in soft bags.

Of the total buffycoat pool (500 mL; 723×109 cells/L), the volume recovered was 350 mL having a cell concentration of 738×10$^9$ cells/L. This gives a platelet recovery of 71.5%, which is lower than the platelet recovery obtained for pentastarch-infused PAS (77±3%), but still significantly higher than PAS alone (65±2%), and comparable to plasma (73±6%).

As is evident from the above, the viscous platelet additive solution infused with pentastarch is at least an equivalent platelet storage solution when compared to plasma, and is superior in several respects. Additionally, the use of a viscous PAS in accordance with the present invention can provide platelet yields that are equivalent or better to those obtained using plasma, and which are significantly better than those obtained using known platelet additive solutions.

Accordingly, the addition of a viscosity increasing agent to a platelet additive solution in accordance with the present invention can provide several potential commercial benefits when compared to known platelet additive solutions, such as improvements in platelet production time and yield, and at the same time provide a storage solution that is comparable or better than plasma. As well, when combined with pathogen-inactivating agents, a better recovery and consequent higher concentration of platelets at the outset could result in less collateral platelet loss due to the pathogen-inactivation process.

We claim:

1. A platelet additive solution (PAS) comprising at least one viscosity increasing agent and platelet additive components, wherein the at least one viscosity increasing agent is hydroxyethyl starch and the viscosity of the solution is between 1.128 and 1.228 centipoise when measured at 37° C.

2. The platelet additive solution according to claim 1, wherein the hydroxyethyl starch comprises pentastarch.

3. The platelet additive solution according to claim 1, wherein the viscosity increasing agent is provided at a concentration effective to yield a platelet additive solution viscosity of about 1.178 centipoise.

4. The platelet additive solution according to claim 1, further comprising at least one energy source, at least one buffering component, at least one chelator, at least one salt and optionally at least one metabolic regulator and/or membrane polarity stabilizing component.

5. The platelet additive solution according to claim 4, wherein the at least one salt is provided at a concentration sufficient to give a PAS osmolality ranging from 250 mOsm to 400 mOsm.

6. The platelet additive solution according to claim 5, wherein the at least one salt is provided at a concentration sufficient to give a PAS osmolality ranging from 270 mOsm to 310 mOsm.

7. The platelet additive solution according to claim 6, wherein the at least one salt is provided at a concentration sufficient to give a PAS osmolality ranging from 290 mOsm to 300 mOsm.

8. The platelet additive solution according to claim 4, comprising 10.0-10.9 mM Na$_3$Citrate, 27.0-32.5 mM NaAcetate, 69.0-115 mM NaCl.

9. The platelet additive solution according to claim 4, wherein the hydroxyethyl starch is pentastarch.

10. The platelet additive solution according to claim 9, further comprising one or more of Na-gluconate, NaH$_2$PO$_4$, Na$_2$HPO$_4$, MgCl$_2$ and KCl.

11. A method of preparing a pooled platelet concentrate comprising suspending prepared platelet pools in a platelet additive solution according to claim 1 and concentrating the platelets.

12. A kit for preparing a platelet concentrate, the kit comprising:
   (i) at least one viscosity increasing agent, and
   (ii) platelet additive solution components,
   wherein the at least one viscosity increasing agent is hydroxyethyl starch and the viscosity increasing agent increases the viscosity of the platelet additive components to between 1.128 centipoise and 1.228 centipoise when measured at 37° C.

13. The kit of claim 12, wherein the at least one viscosity increasing agent and the platelet additive solution components are provided in at least one receptacle capable of containing a liquid or soluble material.

14. The kit of claim 13, wherein the at least one receptacle is selected from the group consisting of a blood bag, a serum bottle, a serum tube, and a vial.

15. The kit of claim 12, wherein the at least one viscosity increasing agent and platelet additive solution components are provided in a sterile aqueous solution.

16. The kit of claim 12, wherein the at least one viscosity increasing agent and platelet additive solution components are provided in a lyophilized form.

17. The kit of claim 12, wherein the at last one viscosity increasing agent and platelet additive solution components are provided as concentrated solutions.

18. The kit of claim 12, wherein the hydroxyethyl starch comprises pentastarch.

19. The kit of claim 12, wherein the platelet additive solution components comprise at least one energy source, at least one buffering component, at least one chelator, at least one salt, and optionally at least one metabolic regulator and/or membrane polarity stabilizing component.

20. The kit of claim 19, wherein the at least one salt is provided at a concentration sufficient to give the platelet additive components in solution an osmolality ranging from 250 mOsm to 400 mOsm.

21. The kit of claim 12, wherein the platelet additive solution components comprise 10.0-10.9 mM Na$_3$Citrate, 27.0-32.5 mM NaAcetate, and 69.0-115 mM NaCl.

22. The kit of claim 12, wherein the at least one viscosity increasing agent increases the viscosity of the platelet additive solution components to about 1.178 centipoise when measured at 37° C.

23. A process for preparing a buffy coat pool in a platelet additive solution comprising hydroxyethyl starch, comprising:
   a) docking a concentrated platelet additive solution and a concentrated solution of hydroxyethyl starch to one or more prepared buffy coats in blood bags;
   b) pooling the buffy coats; and
   c) adding the concentrated platelet additive solution and concentrated solution of hydroxyethyl starch to the pooled buffy coats;
   whereby the mixture of the pooled buffy coats, the concentrated platelet additive solution and the concentrated solution of hydroxyethyl starch has a viscosity of from 1.128 centipoise to 1.228 centipoise when measured at 37° C.

* * * * *